(12) United States Patent
Garland et al.

(10) Patent No.: US 10,638,730 B2
(45) Date of Patent: *May 5, 2020

(54) IMAGING FOR DETERMINATION OF CRUSTACEAN PHYSICAL ATTRIBUTES

(71) Applicant: Clearwater Seafoods Limited Partnership, Bedford, Nova Scotia (CA)

(72) Inventors: John J. Garland, Halifax (CA); Gleb Sekretta, Halifax (CA)

(73) Assignee: Clearwater Seafoods Limited Partnership, Bedford, Nova Scotia (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/146,235

(22) Filed: Sep. 28, 2018

(65) Prior Publication Data

US 2019/0029234 A1 Jan. 31, 2019

Related U.S. Application Data

(63) Continuation of application No. 14/763,409, filed as application No. PCT/CA2013/050930 on Dec. 4, 2013, now Pat. No. 10,111,411.

(Continued)

(51) Int. Cl.
*G06K 9/00* (2006.01)
*A01K 61/90* (2017.01)
(Continued)

(52) U.S. Cl.
CPC .............. *A01K 61/90* (2017.01); *A01K 69/08* (2013.01); *A61B 5/0075* (2013.01);
(Continued)

(58) Field of Classification Search
None
See application file for complete search history.

(56) References Cited

U.S. PATENT DOCUMENTS 6,808,448 B1 10/2004 Kanaya
2006/0124071 A1* 6/2006 Campbell .............. A01K 61/59
119/204

(Continued)

FOREIGN PATENT DOCUMENTS

CN 1181288 A 5/1998
CN 203018326 U 6/2013
(Continued)

OTHER PUBLICATIONS

Predicting Crawfish Molting with Machine Vision Sistler et al. 1995.*
Office Action issued in Chinese Patent Application No. 201380072442.0 dated Feb. 7, 2018 (9 pages), with English translation (11 pages).
O'Halloran and O'Dor, "Molt Cycle of Male Snow Crabs, Chionoecetes Opilio, From Observations of External Features, Setal Changes, and Feeding Behavior", Journal of Crustacean Biology, vol. 8, p. 164-176, 1988 (13 pages).
(Continued)

*Primary Examiner* — Delomia L Gilliard
(74) *Attorney, Agent, or Firm* — McDonnell Boehnen Hulbert and Berghoff LLP

(57) ABSTRACT

The present disclosure relates to imaging for determination of crustacean physical attributes. An image of a shell of a live crustacean is captured and processed to determine a physical attribute of the live crustacean. In an embodiment a characteristic of a pattern indicative of moult stage of the live crustacean is detected, from the captured image. Multiple images may be used in some embodiments, including images of different types such as visible spectrum images, infrared spectrum images, and/or ultraviolet spectrum images.

36 Claims, 5 Drawing Sheets

Related U.S. Application Data

(60) Provisional application No. 61/904,698, filed on Nov. 15, 2013, provisional application No. 61/761,417, filed on Feb. 6, 2013.

(51) Int. Cl.
*G06T 7/00* (2017.01)
*A01K 69/08* (2006.01)
*A61B 5/00* (2006.01)
*G01N 21/956* (2006.01)

(52) U.S. Cl.
CPC ......... *A61B 5/0077* (2013.01); *G01N 21/956* (2013.01); *G06K 9/00* (2013.01); *G06T 7/0004* (2013.01); *A61B 2503/40* (2013.01); *G06T 2207/10016* (2013.01); *G06T 2207/10024* (2013.01); *G06T 2207/10048* (2013.01); *G06T 2207/10152* (2013.01); *G06T 2207/30128* (2013.01)

(56) References Cited

U.S. PATENT DOCUMENTS

| | | | |
|---|---|---|---|
| 2009/0132174 | A1 | 5/2009 | Burke et al. |
| 2010/0272426 | A1* | 10/2010 | Huliyapur Math .... G03B 17/24 396/310 |
| 2011/0028849 | A1 | 2/2011 | Kholodkevich et al. |
| 2014/0168411 | A1* | 6/2014 | Ledet .................. A22C 29/023 348/89 |

FOREIGN PATENT DOCUMENTS

| | | | |
|---|---|---|---|
| EP | 1219175 | A1 | 7/2002 |
| EP | 2425232 | B1 | 1/2013 |
| JP | 2001078659 | A | 3/2001 |
| JP | 2010117177 | | 5/2010 |
| WO | 92/12627 | A1 | 8/1992 |
| WO | 94/03793 | A1 | 2/1994 |
| WO | 2008016309 | | 2/2008 |
| WO | 2008016309 | A1 | 2/2008 |
| WO | 2010145881 | | 12/2010 |
| WO | 2011058529 | | 5/2011 |

OTHER PUBLICATIONS

Office Action issued in New Zealand Patent Application No. 710440 dated Feb. 28, 2018 (5 pages).
Timmermans et al., "Predicting Crawfish Molting With Machine Vision", Journal of the World Aquaculture Society, vol. 26, No. 3, Sep. 1995 (6 pages).
Office Action issued in Chinese Patent Application No. 201380072442.0 dated Aug. 9, 2017 (7 pages), with English translation (13 pages).
Shi Chuancui, "How to Breed Lobsters", Anhui Science and Technology Press, Jul. 31, 2002, pp. 4-5, with English translation (3 pages).
Mai Xianjie, "Science of Prawn Healthy Aquaculture" Jul. 31, 2009, Ocean Press, pp. 33-34, with English translation (5 pages).
Examiner's Report issued in Canadian Patent Application No. 2,898,895 dated Apr. 18, 2017 (4 pages).
Sistler et al., "Predicting crawfish molting with machine vision", American Society of Agriculture Engineers, Dec. 18-20, 1990 (25 pages).
Wallat, Geoffrey K., "Analysis of Skin Color Development in Live Goldfish Using a Color Machine Vision System", North American Journal of Aquaculture, 64(1), 79-84.
Chinese Office Action (including English translation) Chinese Application No. 201380072442.0, dated Dec. 19, 2016, 35 pages in total.
Luo, Yan, "Detection of Shrimp Specification Based on Machine Vision", Installment 1, China's Outstanding Master's Degree dissertation full-text database of Information Technology Services Division, Jun. 15, 2013, 93 pages (English Language Abstract at pp. 10-11).
English Translation of Chinese Search Report, Chinese Application No. 201380072442.0, dated Dec. 19, 2016.
Extended Supplementary European Search Report EP 13 87 4729 dated Sep. 9, 2016 (8 pages).
Harada, et al., A method for the quality assessment of hard-shelled and soft-shelled male snow crab Chionoecetes opilio:, Nippon Suisan Gakkaishi vol. 72, No. 6, pp. 1103-1107, Nov. 2006.
Japanese Office Action dated Jun. 14, 2016 in respect of Japanese Patent Application No. 2015-556351.
International Search Report and Written Opinion for PCT/CA2013/050930 dated Feb. 14, 2014 (8 pages).

* cited by examiner

IMAGING FOR DETERMINATION OF CRUSTACEAN PHYSICAL ATTRIBUTES

CROSS-REFERENCE TO RELATED APPLICATIONS

The present application is a continuation of U.S. patent application Ser. No. 14/763,409, entitled "IMAGING FOR DETERMINATION OF CRUSTACEAN PHYSICAL ATTRIBUTES" and filed Jul. 24, 2015, which is a National Phase application of, and claims the benefit of, International (PCT) Application Serial No. PCT/CA2013/050930, filed on Dec. 4, 2013, which claims priority to U.S. Provisional Patent Application Ser. No. 61/761,417, entitled "DETERMINATION OF CRUSTACEAN MOULT STAGE" and filed Feb. 6, 2013, and U.S. Provisional Patent Application Ser. No. 61/904,698, entitled "IMAGING FOR DETERMINATION OF CRUSTACEAN PHYSICAL ATTRIBUTES" and filed Nov. 15, 2013. The entire contents of each of these applications are incorporated herein by reference.

FIELD OF THE INVENTION

This invention relates generally to determining one or more physical attributes of crustaceans, and in particular to using imaging in determining physical attributes.

BACKGROUND

It is known that many aquatic invertebrates such as crustaceans go through a cycle of moulting, in which an old hard shell is shed and a new larger soft shell is grown. Depending on the stage of the moulting process, a crustacean's internal body, i.e., the "meat" portion of a lobster for example, may occupy a reduced part of the internal volume of the new shell as the internal body grows to occupy the new, larger shell. The internal structure of a crustacean, including its organs, meat and muscle, is undersized in proportion to its new shell after moulting. In order to "fill out" a new, oversized shell after moulting, a crustacean takes on and retains water within its internal structure. As a result, inter-moult crustaceans (hard shell) generally produce high meat yields, while post-moult (soft shell) crustaceans generally produce lower meat yields.

Seafood is often an expensive food product for which a consumer might consider paying a premium. In return, the consumer expects to receive a high quality product that reflects the price paid. For example, consumers will often pay a premium for larger crustaceans, in terms of weight and/or size, and the consumer will generally expect the size of the crustacean to correspond to the amount of meat yielded by the crustacean. However, due to variances in moult stage, a larger post-moult crustacean might not yield any more meat than a smaller pre-moult or inter-moult crustacean. Beyond meat yield or "meatedness", the moult state of a crustacean can also be indicative of health, enabling a seafood processor to assess anticipated mortality rates during storage and/or shipment of crustaceans.

Inter-moult crustaceans can often be identified by their shell hardness. However, this measure is unreliable as a means to determine meat yields and is difficult to implement as a non-invasive measure on a production line. Other attempts at sensing systems employing ultrasound or x-ray scanning systems have proven difficult to implement and have failed to accurately distinguish between different shell hardnesses and/or different meat yields.

Other methods used in determining moult stage include blood protein analysis and pleopod staging. Both of these methods are invasive, and are typically applied only to a subsample of a crustacean harvest or shipment. These methods also require specialised training to properly interpret results that would accurately determine moult stage or meat yield.

There are also other physical attributes of individual crustaceans that are often measured or otherwise determined manually. These include carapace length for lobster, a measurement which is often used for determining the size of a lobster and which is also used within harvesting regulations for minimum allowable legal sized lobster (for example, 80-85 mm carapace length depending on the fishing district), cracked or damaged exoskeletons, missing or broken legs, gender, and shell morphometrics such as various claw, body and/or tail measurements.

SUMMARY

According to an embodiment, an apparatus includes a camera to capture an image of a shell of a live crustacean; and a pattern detector, operatively coupled to the camera, to detect from the captured image a characteristic of a pattern indicative of moult stage of the live crustacean.

In an embodiment, the image is a visible spectrum image of the live crustacean.

In an embodiment, the image is an infrared spectrum image of the live crustacean.

In an embodiment, the image is an ultraviolet spectrum image of the live crustacean.

In an embodiment, the pattern detector is further operable to detect a characteristic of a pattern indicative of moult stage of the live crustacean from a further image of the live crustacean captured by the camera.

In an embodiment, the pattern for the further image is different from the pattern for the image.

In an embodiment, the camera is a camera that has been modified to remove an infrared filter.

In an embodiment, the camera has been further modified to include a visible light filter.

In an embodiment, the pattern detector is a processing device to execute vision detection software.

In an embodiment, the apparatus also includes an illumination source to illuminate the live crustacean.

In an embodiment, the illumination source provides one or more of: visible, infrared, and ultraviolet spectral components.

In an embodiment, the illumination source is operatively coupled to the camera, and the camera controls the illumination source to illuminate the live crustacean.

In an embodiment, the camera controls the illumination source to illuminate the live crustacean when the image is to be captured.

In an embodiment, the camera controls the illumination source to illuminate the live crustacean only under certain operating conditions.

In an embodiment, the illumination source is a flash of the camera.

In an embodiment, the apparatus also includes a power source operatively coupled to provide power to the camera and to the pattern detector.

In an embodiment, the apparatus also includes a controller, operatively coupled to the pattern detector, to control subsequent handling of the live crustacean based on the detection.

In an embodiment, the subsequent handling includes one or more of: grading of the live crustacean; screening out lower quality crustaceans; allowing or blocking entry of the live crustacean into a trap.

In an embodiment, the apparatus is implemented in one or more of: a conveyor size grading system to determine moult stage or quality of the live crustacean; a boat or plant environment, wherein the live crustacean is placed under the camera and a response as to its quality or moult stage is provided by the pattern detector; a packing area, wherein the live crustacean can be viewed by packers on a monitor to screen out lower quality crustaceans while packing a box for shipment; a mobile phone to detect quality and/or moult stage, wherein the camera comprises a built-in camera of the mobile phone; a hand held device; a trap that denies entry to lower quality live crustaceans based on the determination by the pattern detector.

In an embodiment, the pattern detector is operable to receive a plurality of images, including the captured image, captured by the camera, and to detect the characteristic of the pattern indicative of moult stage of the live crustacean based on the plurality of images.

In an embodiment, the plurality of images includes images of different types.

In an embodiment, the apparatus also includes a switchable filter comprising a plurality of light filters that enable the camera to capture the images of the different types.

In an embodiment, the plurality of light filters are movable into and out of an imaging light path between the camera and the live crustacean.

In an embodiment, the plurality of light filters are movable into and out of an illumination light path between an illumination source and the live crustacean.

The characteristic of a pattern indicative of moult stage could include one or more of: absence/presence of a predetermined pattern in the captured image of the shell; brightness of the predetermined pattern in the captured image of the shell; and brightness of an overall pattern of the shell in the captured image of the shell.

The apparatus could also include a Global Positioning System (GPS) receiver to provide location information to be associated with the captured image A method includes: capturing an image of a shell of a live crustacean; and detecting from the captured image a characteristic of a pattern indicative of moult stage of the live crustacean.

In an embodiment, the capturing involves capturing a visible spectrum image of the live crustacean.

In an embodiment, the capturing involves capturing an infrared spectrum image of the live crustacean.

In an embodiment, the capturing involves capturing an ultraviolet spectrum image of the live crustacean.

In an embodiment, the method also includes capturing a further image of the live crustacean; detecting from the further image a characteristic of a pattern indicative of moult stage of the live crustacean.

In an embodiment, the pattern for the further image is different from the pattern for the image.

In an embodiment, the capturing involves capturing the infrared image with a camera that has been modified to remove an infrared filter.

In an embodiment, the capturing involves capturing the infrared image with a camera that has been modified to remove an infrared filter and to include a visible light filter.

In an embodiment, the detecting involves training vision detection software to detect the characteristic of the pattern.

In an embodiment, the method also includes illuminating the live crustacean.

In an embodiment, the illuminating involves illuminating the live crustacean with one or more of: visible, infrared, and ultraviolet spectral components.

In an embodiment, the method also includes controlling subsequent handling of the live crustacean based on the detecting.

In an embodiment, the subsequent handling involves one or more of: grading of the live crustacean; screening out lower quality crustaceans; allowing or blocking entry of the live crustacean into a trap.

In an embodiment, the capturing involves capturing a plurality of images, including the captured image, and the detecting involves detecting the characteristic of the pattern indicative of moult stage of the live crustacean based on the plurality of images.

In an embodiment, the plurality of images include images of different types.

In an embodiment, the method also includes moving a plurality of light filters into and out of a light path to enable capturing of the images of the different types.

In an embodiment, the light path is an imaging light path between the camera and the live crustacean.

In an embodiment, the light path is an illumination light path between an illumination source and the live crustacean.

The characteristic could include one or more of: absence/presence of a predetermined pattern in the captured image of the shell; brightness of the predetermined pattern in the captured image of the shell; and brightness of an overall pattern of the shell in the captured image of the shell.

The method could also include: collecting location information; associating the location information with the captured image.

Also disclosed is use of a machine vision system to capture an image of a live crustacean and detect from the captured image a characteristic of a pattern indicative of moult stage of the live crustacean.

There is also provided an apparatus comprising: a camera to capture an image of a shell of a live crustacean; an image processor, operatively coupled to the camera, to process the captured image to determine a physical attribute of the live crustacean.

In some embodiments, the physical attribute includes any one or more of: moult stage; carapace length; shell defects; missing or broken legs; gender; shell morphometrics.

In some embodiments, the image includes a visible spectrum image of the live crustacean.

In some embodiments, the image includes an infrared spectrum image of the live crustacean.

In some embodiments, the image includes an ultraviolet spectrum image of the live crustacean.

In some embodiments, the image processor is further operable to determine a physical attribute of the live crustacean from a further image of the live crustacean captured by the camera.

In some embodiments, the physical attribute determined from the further image is different from the physical attributed determined from the image.

In some embodiments, the camera is a camera that has been modified to remove an infrared filter.

In some embodiments, the camera has been further modified to include a visible light filter.

In some embodiments, the image processor includes a processing device to execute vision detection software.

In some embodiments, the apparatus also includes an illumination source to illuminate the live crustacean.

In some embodiments, the illumination source provides one or more of: visible, infrared, and ultraviolet spectral components.

In some embodiments, the illumination source is operatively coupled to the camera, and the camera controls the illumination source to illuminate the live crustacean.

In some embodiments, the camera controls the illumination source to illuminate the live crustacean when the image is to be captured.

In some embodiments, the camera controls the illumination source to illuminate the live crustacean only under certain operating conditions.

In some embodiments, the illumination source includes a flash of the camera.

In some embodiments, the apparatus also includes a power source operatively coupled to provide power to the camera and to the pattern detector.

In some embodiments, the apparatus also includes a controller, operatively coupled to the image processor, to control subsequent handling of the live crustacean based on the determined physical attribute.

In some embodiments, the subsequent handling includes one or more of: grading of the live crustacean; screening out lower quality crustaceans; allowing or blocking entry of the live crustacean into a trap.

In some embodiments, the apparatus is implemented in one or more of: a conveyor size grading system to determine moult stage or quality of the live crustacean; a boat or plant environment, wherein the live crustacean is placed under the camera and a response as to its determined physical attribute is provided by the image processor; a packing area, wherein the live crustacean can be viewed by packers on a monitor to screen out lower quality crustaceans while packing a box for shipment; a mobile phone, wherein the camera comprises a built-in camera of the mobile phone; a hand held device; a trap that denies entry to lower quality live crustaceans based on the determination by the image processor.

In some embodiments, the image processor is operable to receive a plurality of images, including the captured image, captured by the camera, and to determine the physical attribute of the live crustacean based on the plurality of images.

In some embodiments, the plurality of images include images of different types.

In some embodiments, the apparatus also includes a switchable filter comprising a plurality of light filters that enable the camera to capture the images of the different types.

In some embodiments, the plurality of light filters are movable into and out of an imaging light path between the camera and the live crustacean.

In some embodiments, the plurality of light filters are movable into and out of an illumination light path between an illumination source and the live crustacean.

The apparatus could also include a GPS receiver to provide location information to be associated with the captured image.

A method includes: capturing an image of a shell of a live crustacean; and processing the captured image to determine a physical attribute of the live crustacean.

In some embodiments, the physical attribute comprising any one or more of: moult stage; carapace length; shell defects; missing or broken legs; gender; shell morphometrics.

In some embodiments, the capturing involves capturing a visible spectrum image of the live crustacean.

In some embodiments, the capturing involves capturing an infrared spectrum image of the live crustacean.

In some embodiments, the capturing involves capturing an ultraviolet spectrum image of the live crustacean.

In some embodiments, the method also involves: capturing a further image of the live crustacean; determining a physical attribute of the live crustacean from the further image of the live crustacean captured by the camera.

In some embodiments, the physical attribute determined from the further image is different from the physical attributed determined from the image.

In some embodiments, the capturing involves capturing the infrared image with a camera that has been modified to remove an infrared filter.

In some embodiments, the capturing involves capturing the infrared image with a camera that has been modified to remove an infrared filter and to include a visible light filter.

In some embodiments, the detecting involves training vision detection software to detect a characteristic in the capture image that is indicative of the physical attribute.

In some embodiments, the method also includes illuminating the live crustacean.

In some embodiments, the illuminating involves illuminating the live crustacean with one or more of: visible, infrared, and ultraviolet spectral components.

In some embodiments, the method also involves controlling subsequent handling of the live crustacean based on the detecting.

In some embodiments, the subsequent handling includes one or more of: grading of the live crustacean; screening out lower quality crustaceans; allowing or blocking entry of the live crustacean into a trap.

In some embodiments, the capturing involves capturing a plurality of images, including the captured image, and the processing involves determining the physical attribute of the live crustacean based on the plurality of images.

In some embodiments, the plurality of images include images of different types.

In some embodiments, the method also involves moving a plurality of light filters into and out of a light path to enable capturing of the images of the different types.

In some embodiments, the light path includes an imaging light path between the camera and the live crustacean.

In some embodiments, the light path includes an illumination light path between an illumination source and the live crustacean.

A method could also include: collecting location information; associating the location information with the captured image.

Another aspect provides a use of a machine vision system to capture an image of a live crustacean and determine from the captured image a physical attribute of the live crustacean.

In some embodiments, the apparatus also includes: a GPS receiver to provide location information to be associated with the captured image.

In some embodiments, the method also includes: collecting location information; associating the location information with the captured image.

Other aspects and features of embodiments of the present invention will become apparent to those ordinarily skilled in the art upon review of the following description.

BRIEF DESCRIPTION OF THE DRAWINGS

Examples of embodiments of the invention will now be described in greater detail with reference to the accompanying drawings.

DETAILED DESCRIPTION

Figure 1:
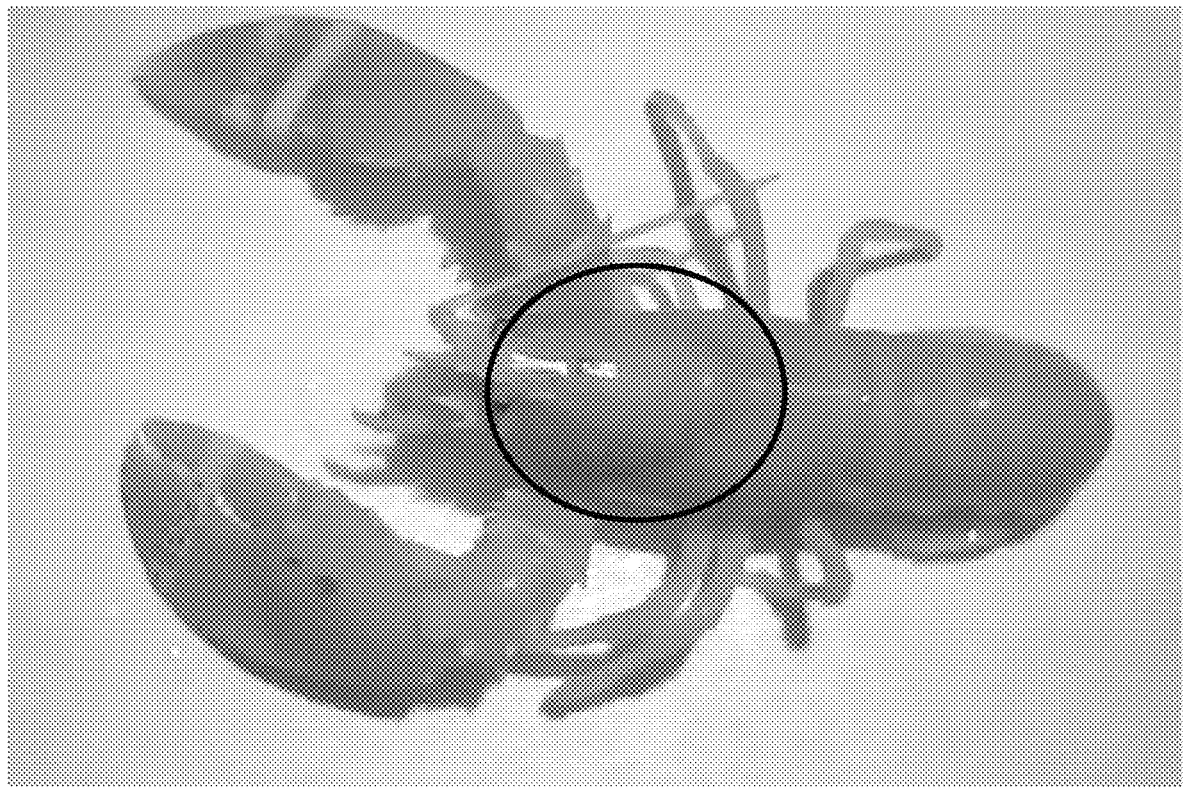
FIG. 1 is an infrared image of a low blood protein lobster.

A crustacean's moult stage relates to the commercial quality of the animal, in terms of meat yield and also the fitness of the animal for storage and shipment in its live state. Determination of moult stage can thus be useful in the seafood industry for various purposes.

In the present disclosure, the lobster *Homarus americanus* is used as an illustrative example species. Embodiments disclosed herein could be applied to not only this example species, but could also or instead be applied to other crustaceans such as other lobster species and/or crabs, for instance.

A lobster must moult its shell in order to grow, since the shell is a rigid outer exoskeleton that does not expand to accommodate growth. To grow, the lobster creates a new shell underneath the exoskeleton. This new shell is relatively pliable and soft. Growth of the new shell occurs during an active pre-moult stage and can take several months, typically beginning in late May and completing in August/September for *Homarus americanus*.

During the new shell development phase, various physical changes occur to the exoskeleton. These changes include the mobilization of calcium from the existing hard shell to form gastroliths on the sides of the stomach as a calcium mineral reserve for the new shell, as well as colour variations in the outer surface of the shell as it proceeds through pre-moult.

Once the new, internally developed shell is complete, the lobster enters an active moulting stage known as ecdysis. During ecdysis, the lobster splits the old shell open at various seams using hydrostatic pressure from the absorption of seawater into its body, as well as physical force as the lobster pulls itself out of the old shell. Ecdysis typically takes approximately 30 minutes to complete. Once out of the old shell, the new soft and previously internal shell becomes the exoskeleton. The lobster continues to absorb water to produce hydrostatic pressure against the new exoskeleton to stretch it to a larger size. The moulting process will cause the lobster to grow in size by approximately 25%. The newly stretched exoskeleton then begins to harden over the course of several months from August to November. During this time, the lobster completes the hardening of the shell and begins to grow the soft internal tissues to fill out the new larger shell.

The moult stages include ecdysis, which as described above is the actual process of shedding the old shell. The next moult stage is post-moult, in which the lobster is hardening its new shell and growing soft tissues to fit into the new shell. This stage is also known as the moult recovery stage. The next stage is inter-moult, in which a lobster has completed moult recovery, has a relatively hard shell, and is fully meated. The next stage is pre-moult, in which a fully meated lobster begins the process of preparing a new shell for the next ecdysis event. Advanced pre-moult is also known as active pre-moult, in which significant energy is being committed by the lobster towards preparing for ecdysis. The lobster then enters ecdysis and the cycle begins once again.

In the seafood industry, moult stages are categorized as they relate to lobster quality, which is measured by both the meatedness of the lobsters as well as their health or fitness levels for standard industry practices of storage and shipment in a live state. To that end, industry has adopted several methods for determining moult stages of lobsters with the intention of determining the quality of the lobsters with respect to meatedness and fitness.

Perhaps the two most commonly accepted methods for determining moult stage and lobster quality are blood protein analysis and pleopod staging.

Blood protein analysis often involves using a refractometer to measure a sample of blood. Blood protein concentration relates directly to meat yield in a live lobster, and thus can be a valuable indicator of lobster quality and can also be indirectly used to determine moult stage. This method is in widespread use in the lobster industry, but is often completed on only a sample of lobsters from a harvest or shipment group to get an average reading of the overall group. The sampling approach is due to the invasive nature of the test, in which blood must be extracted and placed on a refractometer to get the protein concentration. This type of test therefore is not suitable for moult stage determination on an individual basis, for every animal in a harvest or shipment or in a production setting, for example.

Pleopod staging is often undertaken by trained biologists who take a swimmeret or pleopod from the ventral tail section of a lobster and observe, with a low power light microscope, changes in the muscle tissue within the pleopod. These changes in the muscle tissue indicate at which stage the lobster currently is in the moult cycle. This method is precise, but invasive and complicated. As with blood protein analysis, it is feasible to assess only a subset or sample of a harvest or shipment group of lobsters for an overall summary of the group.

There can be a great degree of variability between lobsters within the same harvest or shipment, and therefore sampling methods of determining lobster quality and moult stage, such as blood protein analysis and pleopod staging, do not address the issue of identifying individual lower quality lobsters within a harvest or shipment. If individual lower quality lobsters can be identified, then they can be separated out from a harvest or shipment that is destined for the premium live market, for example. What has been lacking in conventional methods is a robust, accurate method for determining moult stage and therefore lobster quality with a non-invasive method and with specificity or "granularity" to determine moult stage for each individual lobster in a harvest or shipment.

Changes in the shell condition could be one possible indicator of differences in moult stages in lobsters, since there has been some evidence to suggest that the shell undergoes continuous changes from the post-moult stage through to the active pre-moult stage. Shell thickness characteristics are likely to change from the post-moult stage to the inter-moult stage, as the lobster continues to harden the shell. However, measuring shell hardness through squeezing each lobster or measuring the force to flex the shell have proven unreliable in looking for correlations to meatedness. For example, there appear to be circumstances in which softer shelled lobsters can still be fully meated, and hard shell lobsters not fully meated.

In accordance with an embodiment disclosed herein, infrared imaging was used to test shell condition in post-moult versus inter-moult lobsters and in an effort to see structural differences in the shell. Infrared imaging could reveal differences between low and high meated lobsters in correlations or visual cues in the infrared spectrum that are related to blood protein concentrations. A trial involved infrared imaging of lobsters which had been pre-sampled to determine blood protein concentrations. It was discovered that there was a section of the cephalothorax of the lobster (the body's shell) where the head and thorax segments are fused on crustaceans, in which infrared images reveal a dark band present in post-moult, low blood protein lobsters that is not present in inter-moult, high blood protein lobsters. It appeared that the thickness and intensity of this IR visible band decreased with increasing blood protein. Using vision detection software trained on the dark band, the software was able to detect and distinguish low blood protein lobsters from other lobsters with 100% accuracy. Actual accuracy could be lower in other embodiments.

For the purposes of the above-referenced trial, lobsters with blood protein concentrations below 27 mg/mL were labeled as low, lobsters greater than 27 mg/mL but less than 50 mg/mL were labeled as medium and lobsters greater than 50 mg/mL were labeled as high, but a single threshold was used to distinguish the low brood protein concentration lobsters from the others based on presence or absence of the dark band in the infrared images. Multiple thresholds could be used to distinguish between the low, medium, and high blood protein concentration lobsters in this example, based on gradual fading of the dark band with increasing blood protein concentration.

Figure 2:
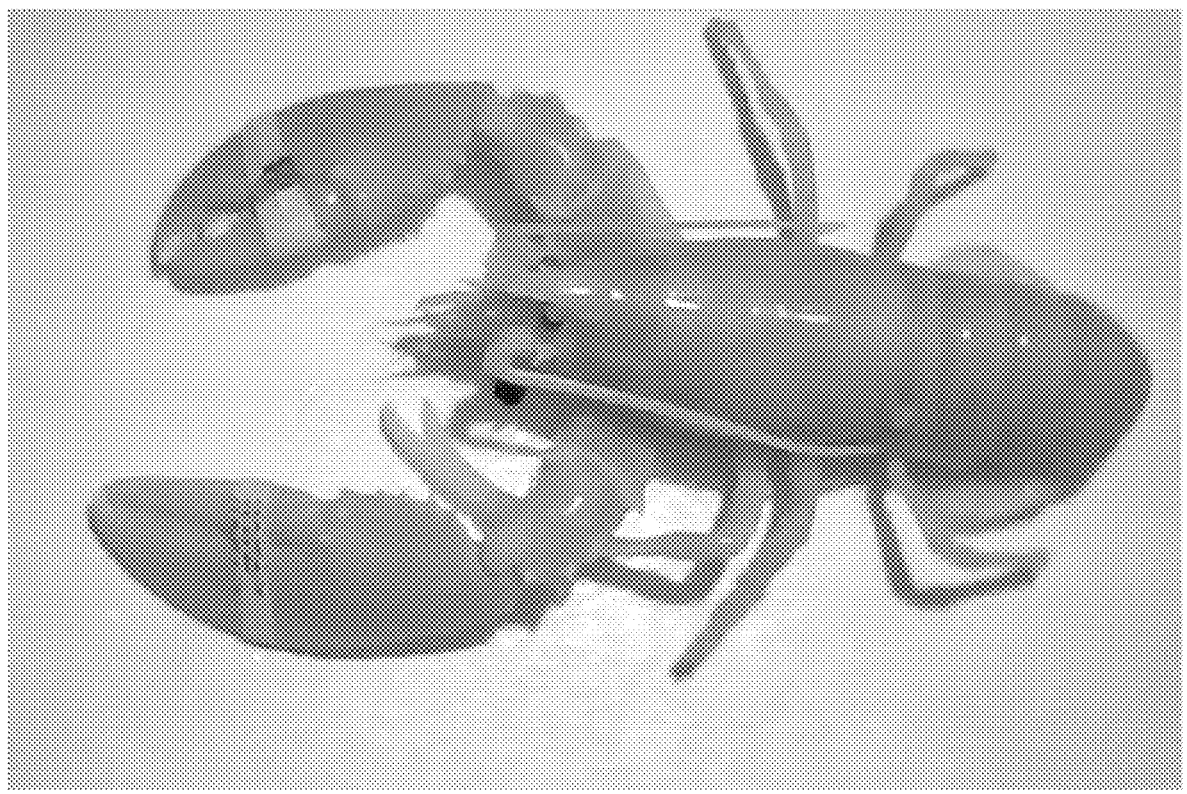
FIG. 2 is an infrared image of a high blood protein lobster.

FIG. 1 is an infrared image of a low blood protein lobster, and FIG. 2 is an infrared image of a high blood protein lobster. A distinct dark band is visible inside the circle in the image of the low blood protein lobster in FIG. 1, but is absent in the image of the high blood protein lobster in FIG. 2.

As noted above, the body shell of a lobster is called a cephalothorax, which means it is both the head and thorax fused together. Where the head and thorax meet and are fused, there is a ridge which is plainly visible but which does not appear to change with the lobster's quality or moult stage when viewed with the naked eye. However, in the infrared spectrum, the fusion ridge varies remarkably between low and high meat yield lobsters. Low blood protein/low meat yield lobsters show up in infrared images with a distinct dark band at the fusion ridge, and this band is not present in the high blood protein/higher meat yield or fully meated lobsters. Vision detection software was used in the above-referenced trial to detect the band and differentiate between low and high meat yield lobsters.

Figure 3:
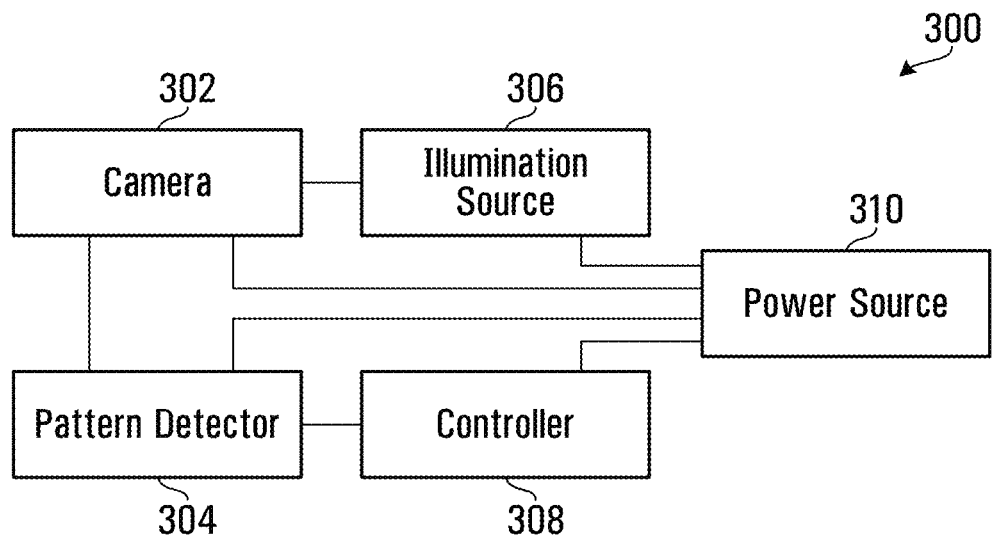
FIG. 3 is a block diagram illustrating an example apparatus.

FIG. 3 is a block diagram illustrating an example apparatus. The example apparatus 300 includes a camera 302, a pattern detector 304, an illumination source 306, a controller 308, and a power source 310, interconnected as shown. It should be appreciated that the example apparatus 300, as well as the contents of the other drawings, are intended solely for illustrative purposes, and that the present disclosure is in no way limited to the particular examples explicitly shown in the drawings. For example, in other embodiments, an apparatus could include further, fewer, and/or different components than those shown in FIG. 3. A system or apparatus in which or in conjunction with which the example apparatus 300 is implemented could also include additional components which are not shown in FIG. 3.

The camera 302 could be implemented in any of various ways. For example, this component could be a visible spectrum camera designed to capture images in the visible spectrum, or a specialized camera that is designed to capture images in the infrared spectrum or the ultraviolet spectrum. Many cameras that are intended to capture images in the visible spectrum include an infrared filter that blocks infrared wavelengths, and such a camera that has been modified to remove the infrared filter could be used as the camera 302. In modifying such a camera, a visible light filter that blocks visible light and/or a filter that passes only infrared wavelengths could be added to improve infrared image quality. A visible spectrum camera could similarly be modified to capture ultraviolet images by adding a visible light filter and/or a filter that passes only ultraviolet wavelengths, for example.

Although FIG. 3 shows a camera at 302, multiple cameras could be provided. For example, characteristics of shell patterns might be more prominent in visible spectrum, infrared, or ultraviolet images. Multiple types of images could be used in determining moult stage as disclosed herein, and could be captured by multiple cameras. Multiple image type capability could also or instead be provided using multiple illumination sources 306.

Another possible implementation to provide for capture of multiple types of images could involve a single camera 302 with a switchable light filter. Such a switchable filter could be provided on or in the camera 302, as a separate component between the camera and an imaging target, on or in the illumination source 306, or as a separate component between the imaging light source and the imaging target, for example, where the illumination source provides broadband light in multiple spectra. For example, a switchable filter could include a visible spectrum filter, an infrared spectrum filter, and an ultraviolet spectrum filter, with different combinations of filters being moved into and out of a light path depending on the type of image to be captured. Filtering could be used in an imaging light path between the camera 302 and an imaging target and/or in an illumination light path between the illumination source 306 and the imaging target, to enable the camera 302 to capture images of different types.

In an embodiment, the pattern detector 304 could be implemented using an element that executes vision software stored in one or more non-transitory memory devices (not shown), such as a solid-state memory device or a memory device that uses movable and/or even removable storage media. Microprocessors, Application Specific Integrated Circuits (ASICs), Field Programmable Gate Arrays (FPGAs), and Programmable Logic Devices (PLDs) are examples of processing devices that could be used to execute software. In general, the pattern detector 304 could be implemented using hardware, firmware, one or more processing devices that execute software, or some combination thereof. The camera 302 and the pattern detector 304 could be parts of the same machine vision system in one possible implementation.

The illumination source 306 could be, for example, an incandescent light that provides both visible and infrared spectral components. Depending on the imaging targets (i.e., live crustaceans) and/or the operating environment of the example apparatus 300, the illumination source 306 might not be provided. For example, the example apparatus 300 might be implemented in an operating environment where sufficient illumination is provided by other light sources. An imaging target might also or instead emit black body radiation that is sufficient for image capture by camera 302 where infrared imaging is used. In an embodiment, the illumination source 306 is a camera flash that is controlled by the camera 302 to illuminate an imaging target each time an image is to be captured or possibly only under certain operating conditions. In some embodiments, the illumination source 306 could be a broadband light source with a switchable filter.

The controller 308 could be implemented in any of various ways, and its structure would be at least partly implementation-dependent. In some embodiments, the controller 308 controls image capture by the camera 302, and the controller could also or instead control the illumination source 306 and/or switchable filtering. In order to avoid congestion in the drawing, connections between the controller 308 and the camera 302 and/or the illumination source 306 have not been shown, but the controller could be operatively coupled to the camera and/or the illumination source in some embodiments.

Based on a determination of moult stage as described herein, any of various actions could be taken in some embodiments, and the controller 308 could be involved in those actions. For instance, the controller 308 could be provided in the example apparatus 300 to control a sorting station on a lobster processing line. In some embodiments, the controller 308 could be part of a moult stage determination apparatus such as 300 but provide outputs to an external component, for example. Thus, a moult stage determination apparatus 300 could include an internal controller 308 and also communicate with an external controller. Although the controller 308 is shown as a component of the example apparatus 300, the controller could actually include an internal controller and/or and external controller. In embodiments involving an external controller, a moult stage determining apparatus such as the example apparatus 300 would include some sort of interface or connection to the external controller. The type and structure of this interface or connection would be implementation-dependent, and compatible with the external controller or other components through which the apparatus communicates with the external controller.

A moult stage determination apparatus such as the example apparatus 300 could be self-powered by a power source 310 such as a battery. In some embodiments, such as in a processing plant implementation, external power might be available.

In operation, the camera 302 captures an image of a shell of a live crustacean, and the pattern detector 304 is coupled to the camera to detect, from the captured image, characteristics of a pattern that is indicative of moult stage of the live crustacean. As noted above, the camera 302 could include a camera to capture a visible spectrum image of the live crustacean, an infrared camera to capture an infrared spectrum image of the live crustacean, and/or an ultraviolet camera to capture an ultraviolet spectrum image of the live crustacean. Using the dark pattern described above as an illustrative and non-limiting example, the characteristic could be the presence or absence of the pattern in a single-threshold embodiment, or darkness of the pattern relative to multiple thresholds.

In a multiple-image implementation, the pattern detector 304 could detect a characteristic of a pattern indicative of moult stage of the live crustacean from a captured visible spectrum image, a characteristic of a pattern indicative of moult stage of the live crustacean from a captured infrared spectrum image, and/or a characteristic of a pattern indicative of moult stage of the live crustacean from a captured ultraviolet spectrum image. The same or different patterns could be used in visible spectrum, infrared spectrum, and/or ultraviolet spectrum images. For example, the dark band pattern described above is prominent in infrared images, and presence/absence or darkness of that band could be a characteristic that is detected by the pattern detector 304. The same or a different pattern could be prominent in visible spectrum images and a characteristic such as shell pattern color could be detected by the pattern detector 304 in those images. It is also contemplated that different patterns and/or pattern characteristics might be prominent in different images of the same type, and that multiple images, such as multiple infrared images from different angles for instance, could be captured by the camera 302 (or multiple cameras) and subjected to detection by the pattern detector 304.

Another possible multiple-image embodiment could involve capturing multiple images of different types, at substantially the same time and/or in rapid succession, using multiple cameras, multiple illumination sources, and/or multiple light filters. Registration of images taken at substantially the same time, especially if taken with a single camera, would be straightforward. Image processing by the pattern detector 304, such as subtraction of different types of images from each other, could increase the contrast of pattern characteristics for detection. Other types of image processing, such as image filtering, "image math" instead of or in addition to image subtraction, and/or spatial frequency transformations (e.g., Fourier domain filtering), could be performed by the pattern detector 304.

Thus, the pattern detector 304 could receive multiple images captured by the camera 302, and detect a characteristic of a pattern based on those images. The images could be processed separately by the pattern detector 304 for detection of the same or different characteristics of the same or different patterns, or used together (e.g., using image subtraction and/or other image processing) for characteristic detections.

In some embodiments, subsequent handling of the live crustacean is controlled by the controller 308 based on the detection by the pattern detector 304. Such subsequent handling could include one or more of the following, for example: grading of the live crustacean, screening out lower quality crustaceans, and allowing or blocking entry of the live crustacean into a trap.

Figure 4:
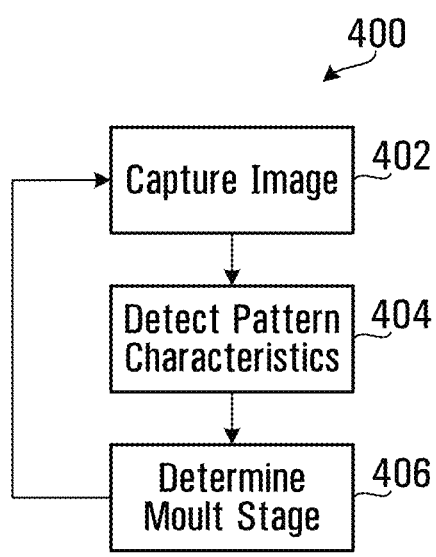
FIG. 4 is a flow diagram illustrating an example method.

FIG. 4 is a flow diagram illustrating an example method 400, which includes capturing, at 402, an image of a shell of a live crustacean and detecting, at 404, from the captured image, a characteristic of a pattern indicative of moult stage of the live crustacean. Moult stage of the crustacean can then be determined, as shown at 406, based on the detection. The example method 400 could be repeated for multiple crustaceans.

Variations of the example method 400 are contemplated. For instance, image capture at 402 and pattern detection at 404 could be ongoing, and need not be performed in the exact sequence shown. Pattern detection for one image at 404 need not necessarily be completed before the next image is captured at 402, for example. Also, at 406, there could be a single threshold for an embodiment to distinguish between lower/higher quality animals based on moult stage, or multiple thresholds for distinguishing between more than two quality grades.

More generally, other embodiments may include similar or different operations, performed in a similar or different order than shown.

Various ways of performing method operations, and at least some variations of the example method 400, may be or become apparent from the foregoing description. The capturing at 402, for example, could involve capturing an infrared image with a camera that has been modified to remove an infrared filter, and has possibly been further modified to include a visible light filter. The pattern characteristic detection at 404 could include training vision detection software to detect the characteristic of the pattern.

Other operations could also be performed, such as illuminating the live crustacean, with one or more of: visible, infrared, and ultraviolet spectral components in some embodiments. Subsequent handling of the live crustacean could be controlled based on the pattern characteristic detection at 404. Grading or screening of the live crustacean as a lower or higher yield/quality crustacean, allowing or blocking entry of the live crustacean into a trap, and/or other subsequent handling operations could be controlled or performed.

The foregoing description relates primarily to determination of crustacean moult stage and/or related quality measures such as meat yield or health based on one or more images of the crustacean shell. Moult stage determination could be implemented in any of various applications.

For example, a machine vision camera could be mounted on a seafood processing plant conveyor size grading system. Images could be captured as each crustacean passes below the camera on a conveyor, and moult stage or quality of each crustacean could then be determined from the captured images. In this type of application, control of subsequent handling of each crustacean could include controlling a sorting station to route higher quality crustaceans and lower quality crustaceans to different destinations for processing. Quality could also or instead be used in grading crustaceans.

Figure 5:
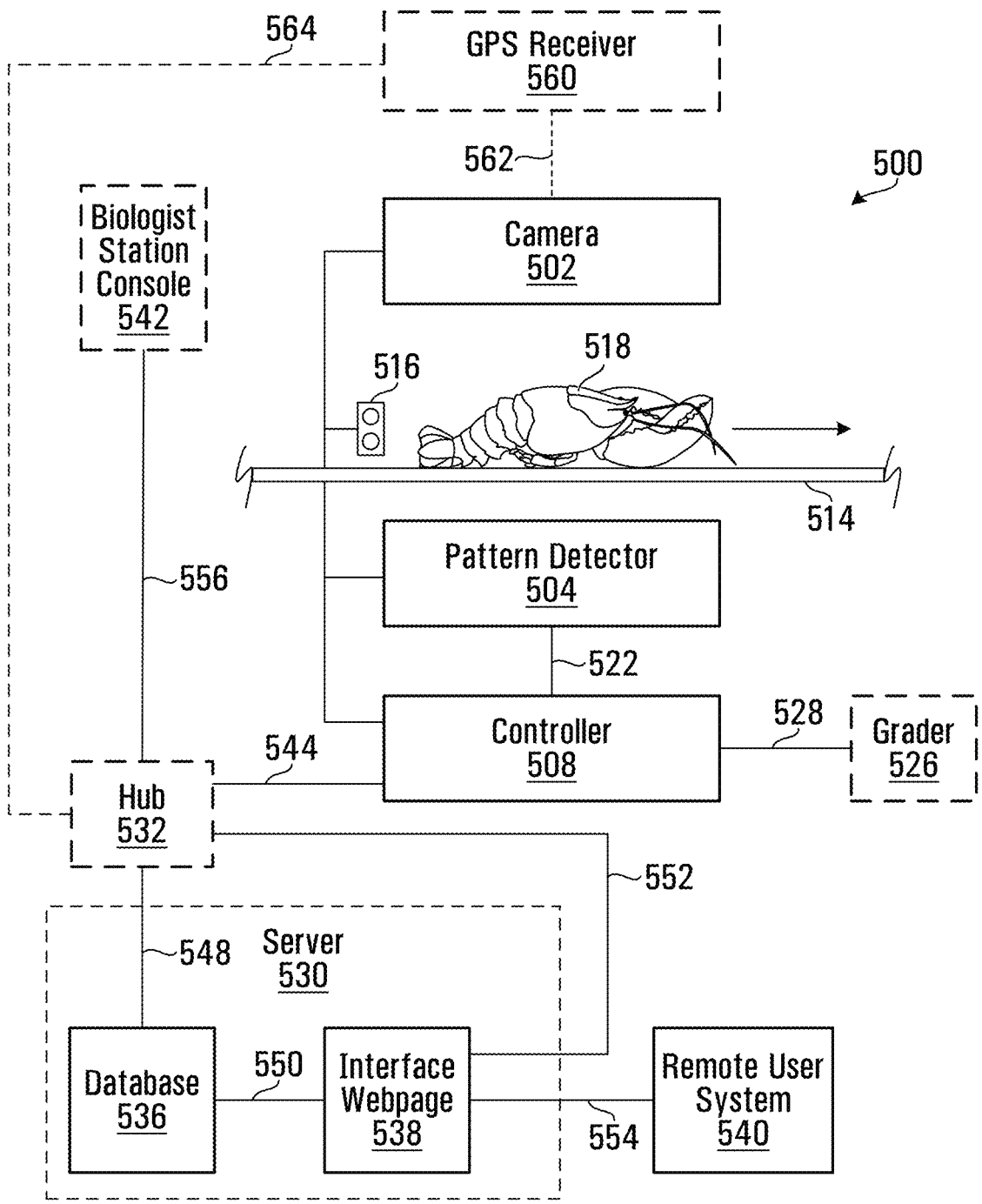
FIG. 5 is a block diagram illustrating an example implementation.

FIG. 5 is a block diagram illustrating an example implementation. The example system 500 includes a camera 502 functionally connected to a pattern detector 504. The camera 502 is located above a conveyor belt 514 that carries a lobster 518 on its top surface in the example shown, although other arrangements are also possible. The pattern detector 504 is shown below the conveyor belt 514, but instead could be co-located with the camera 502 in a machine vision system or located remotely from the camera and/or conveyor belt in other embodiments.

A trigger 516 is located near the top surface of the conveyor belt 514, before the camera 502 relative to a direction of movement of the conveyor belt, such that the lobster 518 trips the trigger 516 as it is moved past the trigger on the conveyor belt. The trigger 516 is functionally connected to the camera 502 and to the pattern detector 504 in the example shown. Depending on relative locations of the camera 502 and the trigger 516, the camera could capture an image of the lobster 518 when the trigger is tripped, or after a certain time delay based on the relative locations and the speed of the conveyor belt 514. Other image capture control mechanisms, by the controller 508 based on a trip signal from the trigger 516 for instance, are also possible. Pattern detection by the pattern detector 504 could also be triggered by the trigger 516, by the camera 502 when an image is captured, or by the controller 508.

In some embodiments, the trigger 516 includes an optical trigger. In general, the trigger 516 may be any type of sensor that detects the arrival of a lobster or other crustacean at a location below or ahead of the camera 502. Although shown separately in FIG. 5, the trigger 516 could potentially be integrated into a single device with the camera 502, the pattern detector 504, or the controller 508.

The camera 502, the pattern detector 504, and the trigger 516 are functionally connected to the controller 508, and the pattern detector connection is shown at 522. In the example system 500, the controller 508 is functionally connected to a grader 526 that is located downstream of the camera 502 with respect to the direction of motion of the conveyor belt 514. The connection between the pattern detector 504 and the controller 508 is shown separately at 522 to represent an output connection through which indications of moult stage determination and/or outputs to control handling of the lobster 518 are provided to the controller by the pattern detector.

In some embodiments, the example system 500 also includes a hub 532 that is functionally connected to the controller 508 at 544. The hub 532 is also functionally connected to a biologist station console 542 at 556 and to a server 530 at 548 and 552.

In some embodiments, the server 530 includes a database 536 functionally connected to the hub 532 at 548, and an interface 538. The interface 538 is functionally connected to the database 536 at 550, and may be functionally connected to the hub 532 through an output 552 of the server 530.

The connection between the hub 532 and the database 536 could be through one or more intermediate components (not shown), such as a listener implemented as a processing device that performs a software algorithm for managing data transfer from the biologist station console 542 and the controller 508, and stores the data in database 536, for instance.

In some embodiments, the interface 538 of the server 530 is implemented as a webpage such as a dynamic personal home page (PHP) webpage.

In some embodiments, a remote user system 540 is functionally connected to the interface 538 of the server 530 at 554.

In operation, as the lobster 518 is moved along by the conveyor belt 514, the trigger 516 is tripped by the lobster. The trigger 516 signals the camera 502 and/or the controller 508 that the lobster 518 is below or approaching the camera. As the lobster 518 passes below the camera 502 on the conveyor belt 514, an image is captured. The pattern detector 504 detects a characteristic of a pattern indicative of moult stage, in the image. In some embodiments, multiple images are captured.

In an embodiment, the characteristic is the presence or absence of the pattern, as determined by the pattern detector 504, which is then used to estimate quality of the lobster 518. An indicator of moult stage and/or quality may be passed on to the controller 508 through an output at 522. Each indicator, and/or a control signal based thereon, may be provided to the grader 526 for sorting purposes.

The proximity of the camera 502 to the lobster 518 can affect the quality of captured images. In general, the distance between the camera 502 and the conveyor belt 514 is an implementation-specific detail that may depend, for example, on the sensitivity of the camera 502 and the speed with which it can adapt to different distances to an image target.

In some embodiments, an RFID (Radio Frequency Identification) tag (not shown) storing information related to an identifier of the lobster 518 is attached to the lobster and the camera 502 or the pattern detector 504 includes an RFID device. The RFID device could then be used to store information relating to moult stage and/or quality of the lobster 518 on the RFID tag. This information could also or instead be transmitted to the server 530 for storage in the database 536. The camera 502, the pattern detector 504, the controller 508, or another component, could also read the lobster identifier from the RFID tag and transmit the identifier to the server 530 so that the image(s) and/or information relating to moult stage/quality can be associated with the individual lobster in the database 536. Information records in the database 536 associated with individual lobsters could be used to provide any of various levels of detail, from individual information to information aggregated across subsets of lobsters or entire harvests, for example.

A Global Positioning System (GPS) receiver 560 could also be provided. The GPS receiver 560 could be functionally connected to the camera 502 through a connection 562, or in some embodiments integrated with the camera or another component of the example system 500. The connection 564 is intended to illustrate that the GPS receiver 560 could also or instead be functionally connected to the server 530 through the hub 532 in the example shown, to provide location data for storage in the database 536. Location data can be associated with the captured image(s) of the lobster 518 to provide a record of where the lobster was harvested. Such location data could also or instead be stored with other information on an RFID tag attached to the lobster 518.

The association of location data from the GPS receiver 560 with the captured image(s) could be handled by any of various components in the example system 500. For example, the camera 502 could include a GPS receiver 560 as an integrated component, and location-image associations might then be an existing function provided by the camera. Such associations could instead be created by the controller 508, elsewhere within a vision system in which the pattern detector 504 is implemented, or at the server 530.

The GPS receiver 560, the camera 502 itself, the controller 508, or another component, could also or instead provide a date and/or time which could similarly be associated with each image. In an embodiment, location, date, and time are all associated with each image, and can be used, for example, for regulatory purposes of confirming whether each lobster 518 was harvested in season and in the correct fishing area. Location, date, and time information could also or instead be used to look at productivity at various times or in various regions.

Each lobster 518 could also or instead be assigned a lot and bin number by the grader 526, and the lot and bin number may also be communicated to the server 530 and/or other components, such as a sorting system which sorts lobsters by lot and bin numbers.

The captured images, identifiers, moult stage, quality, location, date, time, lot number, and bin number are all examples of content that could be stored in the database 536. All of these types of content, or any subset of one or more thereof, could be stored in the database 536, and could potentially be used to sort, separate, or aggregate the stored content. For example, if a lobster dies during storage or shipment, then all information associated with that specific lobster could be retrieved from the database 536 if the stored content includes an identifier. One could also or instead access the database 536 to compile statistics on any of various metrics. Average moult stage and/or quality, moult stage and/or quality distribution, harvest counts, etc., for an entire harvest, harvest area, time period, etc., for instance, could be extracted from the database 536 or determined from data extracted from the database, depending on information that is stored in the database. Such information could be useful for harvest monitoring, conservation, and/or regulatory purposes, for example.

In some embodiments, the database 536 is a MySQL database.

The data in the database 536 can be accessed by the remote user system 540 on the internet via the interface 538 using the input/output 554.

In some embodiments, the remote user system 540 can send instructions to the controller 508, through the hub 532 and its connection to the controller.

In some embodiments, the controller 508 is implemented in a personal computer. Vision detection software could be executed in the same computer to implement the pattern detector 504 in some embodiments.

The biologist station console 542 could allow a biologist or other qualified technician or user to enter pertinent biological data from sampled lobsters, which data can then be sent to and stored in the database 536. The biological data could include blood protein concentration from a sampled lobster, for example, which can provide continuous calibration data for the camera 502 and the pattern detector 504. For example, if the blood protein concentration of a sampled lobster is determined by another system or device (not shown) and entered into the database 536 by a biologist using the biologist station console 542, then the sampled lobster can be placed on the conveyor belt 514 and passed below the camera 502 as a calibration lobster, to confirm that image capture and pattern detection are operating properly. Adjustments to the camera 502 and/or the pattern detector 504 could be made if there is any discrepancy between a determination as made by the pattern detector and the determination expected based on the blood protein concentration.

The biologist is also able to view results and reports from the interface 538 from the biologist station console 542.

The interface 538 provides user-initiated access to the database 536 in one embodiment. Automated reporting, to transmit data from the database 536 to an external component such as a regulatory agency, for example, is also contemplated. A harvest vessel or production facility could report collected data at certain time intervals and/or certain times of day, for instance. Thus, "pull" data access to access data in the database 536 on demand, and/or automatic reporting or other "push" access mechanisms, could be supported.

FIG. 5 relates to an example implementation as part of an automated processing line. Another possible application could involve mounting a machine vision camera on a boat or in a plant environment. Workers could then manually place a lobster or other crustacean under the camera lens and wait for a response from vision software as to its quality or moult stage. Different actions could then be taken depending on the response. The response could be provided by any of various forms of indicators, such as a speaker to provide different audible indicators for different moult stages/qualities, lights to provide different visual indicators for different moult stages/qualities, and/or a monitor or other type of display screen to provide more detailed information as to moult stage/quality.

A camera mounted in packing area would enable crustaceans to be viewed by packers on a monitor, for example, to screen out lower quality crustaceans while packing a box for shipment.

Moult stage determination could potentially be implemented in a mobile phone or other hand held device. For example, a mobile phone software application could use a built-in camera (with no IR filter and possibly modified to filter out visible light if infrared imaging is used) to detect quality and/or moult stage. This type of implementation might be useful not only in a seafood processor environment, but also for consumers to determine moult stage and quality prior to purchase. A mobile phone software application could communicate with a server or other component of a seafood processor, distributor, or retailer system, through an HTML website for example, which could verify a consumer's subscription, perform image analysis, and send results back to the phone.

A camera and pattern detector could even be mounted on a trap that denies entry to lower quality lobsters or other crustaceans, thus trapping and landing only higher quality animals. For example, a barrier could be used to block the entrance to a trap until a moult stage/quality determination is made. The barrier would then remain in place if a crustacean attempting to enter the trap is determined to be of lower quality, or moved to permit entry if a crustacean attempting to enter the trap is determined to be of higher quality.

The foregoing description relates primarily to determination of crustacean moult stage based on a characteristic of a pattern such as a dark band at the fusion ridge of the cephalothorax of lobsters. Images of lobsters at various stages of early to late pre-moult reveal that shell brightness also changes within to the IR spectrum. As a lobster progresses through the early to late pre-moult stages, the shell continues to increase in brightness. A threshold brightness level that correlates with the beginning of advanced pre-moult lobsters could also or instead be used as a characteristic to differentiate lobster IR images, and thus lobsters, into early and late pre-moult groups. Therefore, it should be appreciated that another characteristic of a pattern that could also or instead be detected by the pattern detector 304, 504 (FIGS. 3 and 5) or at 404 (FIG. 4) could be brightness of the overall shell pattern and not just the dark band described above.

The moult stage of late pre-moult lobsters (also referred to as advanced pre-moult or "committed to moult" lobsters) cannot be arrested by storing the lobsters in low temperature water. This is why such lobsters can be characterized as "committed to moult", and makes lobsters unsuitable for long term storage. However, early pre-moult lobsters can have their moulting process arrested with cold-water storage, and therefore such lobsters we can be held in long term storage systems without the risk of having them try to moult in storage and die.

A catch of lobsters will have varying proportions of late pre-moult lobsters depending on the season and harvest area. If the proportion of pre-moult lobsters is high, then the entire catch is usually downgraded to short term storage, despite there being acceptable, good quality long term storage lobsters in that catch, due to the mortality risk of storing the proportion of late pre-moult lobsters in that catch. Moult stage determination techniques as disclosed herein could be used to effectively identify and remove only the late pre-moult lobsters from the catch, which would in turn allow a harvester or purchaser to avoid downgrading the entire catch and therefore have at least a portion of the catch available for long term storage.

In some embodiments, a vision system could be trained to detect moult stage from post moult to late pre-moult. Such a vision system could also or instead be trained to detect other physical attributes of individual lobsters that are often measured or otherwise determined manually. These physical attributes could include, for example, any one or more of:

carapace length for lobsters and/or crabs, a measurement often used for determining the size of the lobster or crab and which is used within harvesting regulations for minimum allowable legal sized lobster (80-85 mm carapace length for lobsters, for example, depending on the fishing district);

shell defects such as cracked or damaged exoskeletons, which are often hard to identify within the visible color spectrum due to the "busy" patterns on crustacean shells that can mask damaged and cracked exoskeletons;

missing or broken legs;

gender, based on the smaller width of the tail versus carapace length in male lobsters compared to females with a wider tail width;

shell morphometrics such as various claw, body and/or tail measurements;

such measurements could potentially allow one to associate animals with a specific harvest area in which these unique shell physical attributes are found.

Many of these measurements are included in harvest and biomass surveys for fisheries management purposes. Embodiments disclosed herein, such as a camera and vision system, could allow for the quick and easy collection of such data. In some embodiments, this type of data could be collected on a fishing vessel equipped with a vision system that could be used not only for moult stage and/or physical attribute determination, but also or instead for various purposes such as reporting landed catch, specific statistics on lobsters by area caught (if GPS information is collected at the time of the image scan), etc.

Having the ability to sort by moult stage on a harvest vessel also would allow for an objective individual assessment of each animal so that they could be individually graded by quality type. This level of assessment and grading, on an individual level, could avoid or at least mitigate problems such as: classifying an entire catch as being unsuitable for long term storage even though the catch includes animals that could survive longer term storage and shipping; and lower quality lobsters being sold and distributed to long distance locations resulting in high mortality due to the lobsters' lack of fitness to withstand such a journey. By having quality identified and separated by the harvester on the fishing vessel, a more effective usage strategy can be implemented to reduce mortality that occurs from selling ungraded lobsters. Lower quality lobsters, for example, could be identified and shipped to a processor where they can be processed and packaged, while the higher grade lobsters could be used for live shipment sales which have a higher price and value in the market.

Also, in a distributed or mobile system, data could be collected at any point along a distribution chain from harvest, landed at the wharf, prior to being shipped to a grading facility, at a wholesaler overseas, and/or even by an end consumer interested in such data.

As noted above, shell morphometrics such as various claw, body and/or tail measurements could allow one to associate an animal with a specific harvest area. Individual animals could have unique color and/or morphological patterns or characteristics that could be used to uniquely identify individual animals, for traceability purposes for instance. Color pattern detection could be provided using visible color spectrum camera imaging, but IR images could be better suited to acquiring morphological patterns/characteristics. This type of imaging and detection could play a significant role in being able to implement traceability so that individual lobsters can be identified throughout the distribution system using this type of biometrics. RFID tags as noted above represent one possible individual identification option, and another option that does not involve additional components attached to animals could use such biometrics.

Moult stage is illustrative of one type of physical attribute that could be determined based on imaging of live crustaceans. In embodiments described above with reference to FIGS. 3 to 5, moult stage determination is based on a characteristic, such as a predetermined pattern or an overall shell pattern, in a captured image or multiple captured images. More generally, a physical attribute of a live crustacean could be determined by processing such captured image(s).

Figure 6:
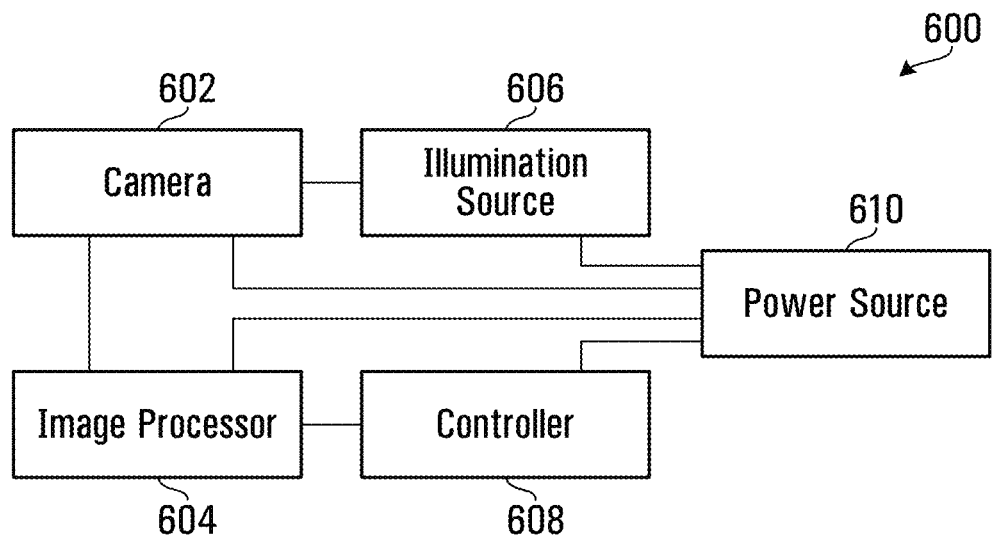
FIG. 6 is a block diagram illustrating another example apparatus.

FIG. 6 is a block diagram illustrating another example apparatus. The example apparatus 600 may be substantially the same as the example apparatus 300 of FIG. 3, with the exception that the example apparatus 600 includes an image processor 604 whereas the example apparatus 300 includes a pattern detector 304. In some embodiments, the image processor 604 may perform pattern detection tasks that are the same as or similar to those performed by the pattern detector 304, although in other embodiments the image processor performs different or additional image processing to determine one or more physical attributes. In other words, the example apparatus 600 could determine moult stage based on a characteristic of a pattern in an image, but it could also or instead determine other physical attributes of live crustaceans such as those noted above.

For instance, to determine carapace length for lobsters, a captured image could be processed by the image processor 604 to identify carapace endpoints, from which the carapace length can be calculated. Gender based on carapace length and/or width of the tail of lobsters, and/or other shell morphometrics such as claw widths and ratios of any of these measurements, could be determined by the image processor 604 in a similar manner based on identifying shell edges, endpoints, and/or other structures in captured. These data could be used to identify lobsters from specific regions, or they could be used to make an inference on the weight of the lobster and allow one to grade lobsters and assign a weight without having to physically weigh each lobster, which can improve the throughput of a size grading system. The image processor 604 could be implemented in a vision system and trained to detect shell defects and/or missing or broken legs.

The example apparatus 600 could otherwise be similar in structure and operation to the example apparatus 300 described in detail herein. Other features that could be provided in the example apparatus 300 could also or instead be provided in the example apparatus 600. For example, measurement points, structures, or patterns might be more prominent in different types of images, and multiple images of different types could be captured. Image processing by the image processor 604 could use multiple images of the same or different types, and various types of processing could be performed. A captured image of one type could be subtracted from a captured image of another type, for instance, to facilitate detection of features or physical attributes of interest in the resultant processed image. Any of various operations could be controlled by the controller 608 based on determined physical attributes.

Figure 7:
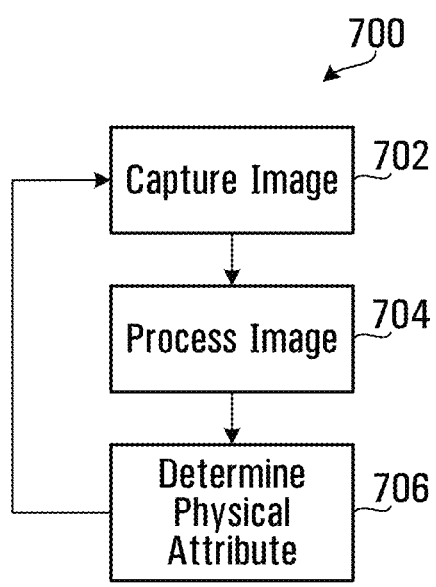
FIG. 7 is a flow diagram illustrating another example method.

FIG. 7 is a flow diagram illustrating another example method 700, which could be substantially similar to the example method 400 shown in FIG. 4 but includes an image processing operation at 704 whereas the example method 400 includes the pattern characteristic detection operation 404, and the example method 700 includes an operation to determine a physical attribute at 706 whereas the example method 400 includes the operation 406 to determine moult stage. The operations 704, 706 could include the operations 404, 406, and/or other operations to determine a physical attribute in addition to or other than moult stage.

Figure 8:
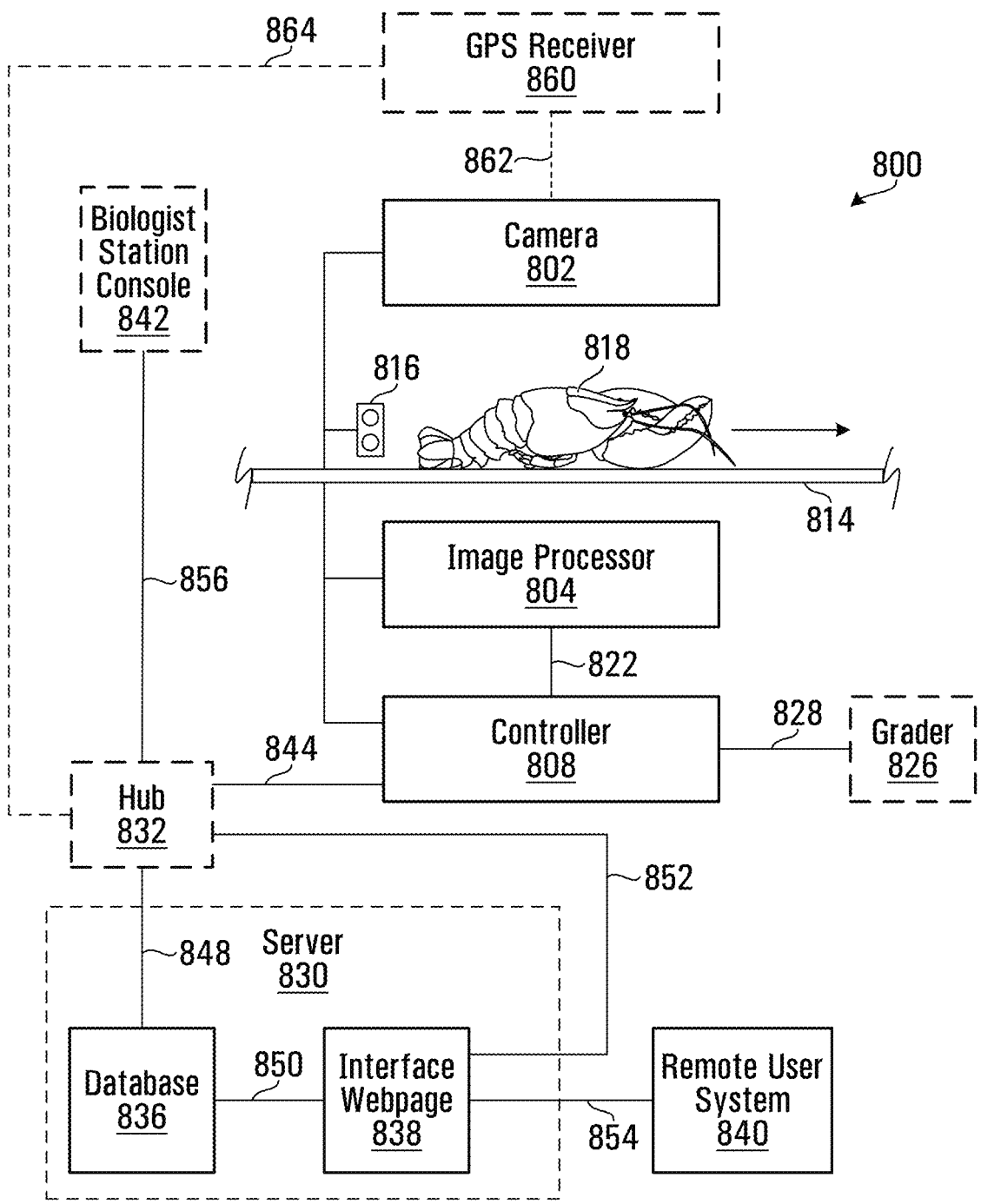
FIG. 8 is a block diagram illustrating another example implementation.

FIG. 8 is a block diagram illustrating another example implementation 800, which could be substantially the same as the example implementation 500 in FIG. 5, but includes an image processor 804 whereas the example implementation 500 includes the pattern detector 808. The example implementations 500, 800 could otherwise be substantially the same in structure and operation.

Physical attribute determination, data collection, data reporting, and/or traceability could be of significant value to various parties. For example, physical attribute determination could be of commercial value to harvesters in that they can be more selective in the animals that are harvested. Higher quality animals could be harvested and sold, and lower quality animals could be identified on board a harvest vessel and thrown back. This could not only increase a harvester's product value and revenue, but also have conservation value as well. Other possible advantages of physical attribute determination, in identifying and sorting different grades of animals, are discussed above. Data collection, data reporting, and traceability could also be of high conservation value and/or scientific value to government or other regulatory agencies, for instance.

What has been described is merely illustrative of the application of principles of embodiments of the invention. Other arrangements and methods can be implemented by those skilled in the art without departing from the scope of the present invention.

For example, the drawings are intended solely for illustrative purposes. Other embodiments might include further, fewer, or additional features, arranged in a similar or different manner than shown.

A predetermined pattern disclosed herein (i.e., a dark band at the fusion ridge of the cephalothorax of lobsters) is also intended solely for the purposes of illustration. There might be additional and/or alternative characteristics that can be used to determine differences between inter-moult lobsters (that can be stored and shipped successfully) and active pre-moult lobsters (that do not store very well and often do not ship very well either). Such a higher level of granularity or resolution in moult stage determination might be possible, for example, if higher contrast infrared images are used. In higher contrast infrared images, the dark band described above and/or other shell characteristics could be more prominent. Other features or physical attributes could similarly be more prominent in different types of images.

Another possible variation of the techniques disclosed herein would be to detect changes in shell color in lobsters that are approaching the active pre-moult stage. Such color changes could be more easily detected in the visible spectrum, the infrared spectrum, or the ultraviolet spectrum, and accordingly moult stage determination could be based on visible, infrared, and/or ultraviolet spectrum image capture and pattern detection. Thus, in general, the techniques disclosed herein could be applied in visible spectrum imaging, infrared imaging, or ultraviolet spectrum imaging, or multiple types of imaging could be used in some embodiments in determining moult stage and/or other physical attributes.

Also, moult stage determination or detection is described above primarily as a pass/fail for higher/lower quality lobsters. However, image resolution might allow three grades of lower, medium and higher quality lobsters, for example, or possibly even more grades, to be distinguished. The disappearance of the dark band under IR imaging as described above, for instance, seems to be gradual and therefore multiple thresholds could be used to suit individual harvest vessel or processing plants' quality sorting objectives.

In addition, although described primarily in the context of methods and systems, other implementations are also contemplated, as instructions stored on a non-transitory computer-readable medium, in the case of pattern detection, image processing, and/or control features for example.

We claim:

1. An apparatus comprising:
a camera to capture an image of a shell of a live crustacean; and
a pattern detector, operatively coupled to the camera, to detect from the captured image a characteristic of a pattern on the shell indicative of moult stage of the live crustacean, and to provide a response as to the moult stage of the live crustacean based on the detection.

2. The apparatus of claim 1, the pattern detector being further operable to detect a characteristic of a pattern indicative of moult stage of the live crustacean from a further image of the live crustacean captured by the camera, the pattern for the further image being different from the pattern for the image.

3. The apparatus of claim 1, the pattern detector comprising a processing device to execute vision detection software.

4. The apparatus of claim 1, further comprising:
a controller, operatively coupled to the pattern detector, to control subsequent handling of the live crustacean based on the detection by the pattern detector.

5. The apparatus of claim 4, wherein the subsequent handling comprises one or more of:
grading of the live crustacean;
screening out lower quality crustaceans;
allowing or blocking entry of the live crustacean into a trap.

6. The apparatus of claim 1, implemented in one or more of:
a conveyor size grading system;
a boat or plant environment, wherein the live crustacean is placed under the camera;
a packing area, wherein the live crustacean can be viewed by packers on a monitor to screen out lower quality crustaceans while packing a box for shipment;
a mobile phone to detect quality and/or moult stage, wherein the camera comprises a built-in camera of the mobile phone;
a hand held device;
a trap that denies entry to lower quality live crustaceans based on the detection by the pattern detector.

7. The apparatus of claim 1, the pattern detector being operable to receive a plurality of images, including the captured image, captured by the camera, and to detect the characteristic of the pattern indicative of moult stage of the live crustacean based on the plurality of images.

8. The apparatus of claim 7, the plurality of images comprising images of different types.

9. The apparatus of claim 1, the characteristic comprising one or more of:
absence/presence of a predetermined pattern in the captured image of the shell;
brightness of the predetermined pattern in the captured image of the shell; and
brightness of an overall pattern of the shell in the captured image of the shell.

10. The apparatus of claim 1, further comprising:
a Global Positioning System (GPS) receiver to provide location information to be associated with the captured image.

11. A method comprising:
capturing an image of a shell of a live crustacean;
detecting from the captured image a characteristic of a pattern on the shell indicative of moult stage of the live crustacean; and
providing a response as to the moult stage of the live crustacean based on the detecting.

12. The method of claim 11, further comprising:
capturing a further image of the live crustacean;
detecting from the further image a characteristic of a pattern indicative of moult stage of the live crustacean, the pattern for the further image being different from the pattern for the image.

13. The method of claim 11, further comprising:
training vision detection software to detect the characteristic of the pattern.

14. The method of claim 11, further comprising:
controlling subsequent handling of the live crustacean based on the detecting.

15. The method of claim 14, wherein the subsequent handling comprises one or more of:
grading of the live crustacean;
screening out lower quality crustaceans;
allowing or blocking entry of the live crustacean into a trap.

16. The method of claim 11,
the capturing comprising capturing a plurality of images, including the captured image,
the detecting comprising detecting the characteristic of the pattern indicative of moult stage of the live crustacean based on the plurality of images.

17. The method of claim 16, the plurality of images comprising images of different types.

18. The method of claim 11, the characteristic comprising one or more of:
absence/presence of a predetermined pattern in the captured image of the shell;
brightness of the predetermined pattern in the captured image of the shell; and
brightness of an overall pattern of the shell in the captured image of the shell.

19. The method of claim 11, further comprising:
collecting location information;
associating the location information with the captured image.

20. Use of a machine vision system to capture an image of a shell of a live crustacean, to detect from the captured image a characteristic of a pattern on the shell indicative of moult stage of the live crustacean, and to provide a response as to the moult stage of the live crustacean based on the detection.

21. The apparatus of claim 1,
the image comprising an infrared spectrum image of the live crustacean, and
the pattern comprising a band at a section of a cephalothorax of the live crustacean.

22. The apparatus of claim 21, the characteristic comprising presence/absence or darkness of the pattern.

23. The apparatus of claim 21, the characteristic comprising darkness of the pattern relative to one or more thresholds.

24. The apparatus of claim 1,
the image comprising an infrared spectrum image of the live crustacean, and
the pattern comprising a band where a head segment and a thorax segment of the live crustacean are fused.

25. The apparatus of claim 24, the characteristic comprising presence/absence or darkness of the pattern.

26. The apparatus of claim 24, the characteristic comprising darkness of the pattern relative to one or more thresholds.

27. The apparatus of claim 1,
the image comprising an infrared spectrum image of the live crustacean, and
the characteristic of the pattern comprising a structural difference in the shell of the live crustacean related to blood protein concentration.

28. The apparatus of claim 1,
the image comprising an infrared spectrum image of the live crustacean, and
the characteristic of the pattern comprising brightness of an overall shell pattern.

29. The method of claim 11,
the image comprising an infrared spectrum image of the live crustacean, and
the pattern comprising a band at a section of a cephalothorax of the live crustacean.

30. The method of claim 29, the characteristic comprising presence/absence or darkness of the pattern.

31. The method of claim 29, the characteristic comprising darkness of the pattern relative to one or more thresholds.

32. The method of claim 11,
the image comprising an infrared spectrum image of the live crustacean, and
the pattern comprising a band where a head segment and a thorax segment of the live crustacean are fused.

33. The method of claim 32, the characteristic comprising presence/absence or darkness of the pattern.

34. The method of claim 32, the characteristic comprising darkness of the pattern relative to one or more thresholds.

35. The method of claim 11,
the image comprising an infrared spectrum image of the live crustacean, and
the characteristic of the pattern comprising a structural difference in the shell of the live crustacean related to blood protein concentration.

36. The method of claim 11,
the image comprising an infrared spectrum image of the live crustacean, and
the characteristic of the pattern comprising brightness of an overall shell pattern.

* * * * *